US011642110B2

(12) United States Patent
Batchelor et al.

(10) Patent No.: US 11,642,110 B2
(45) Date of Patent: *May 9, 2023

(54) LAPAROSCOPIC SURGICAL DEVICE WITH FLARED TUBE

(71) Applicant: GYRUS ACMI, INC., Southborough, MA (US)

(72) Inventors: Kester J. Batchelor, Mound, MN (US); James Faucher, Brookland Park, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 315 days.

This patent is subject to a terminal disclaimer.

(21) Appl. No.: 16/821,566

(22) Filed: Mar. 17, 2020

(65) Prior Publication Data

US 2020/0214683 A1 Jul. 9, 2020

Related U.S. Application Data

(63) Continuation of application No. 15/481,841, filed on Apr. 7, 2017, now Pat. No. 10,631,836.

(Continued)

(51) Int. Cl.
*A61B 17/00* (2006.01)
*A61B 17/28* (2006.01)
(Continued)

(52) U.S. Cl.
CPC ........ *A61B 17/00* (2013.01); *A61B 17/00234* (2013.01); *A61B 17/28* (2013.01);
(Continued)

(58) Field of Classification Search
CPC ... A61B 17/00; A61B 17/00234; A61B 17/28; A61B 17/29; A61B 17/30; A61B 17/50;
(Continued)

(56) References Cited

U.S. PATENT DOCUMENTS

| 1,294,284 A | 2/1919 | Logeman |
| 2,137,710 A | 11/1938 | Anderson |
| (Continued) | | |

FOREIGN PATENT DOCUMENTS

| EP | 0722286 A1 | 7/1996 |
| EP | 3422967 A1 | 1/2019 |
| (Continued) | | |

OTHER PUBLICATIONS

U.S. Appl. No. 15/481,841 U.S. Pat. No. 10,631,836, filed Apr. 7, 2017, Laparoscopic Surgical Device With Flared Tube.

(Continued)

*Primary Examiner* — Richard G Louis
*Assistant Examiner* — Chima U Igboko
(74) *Attorney, Agent, or Firm* — Schwegman Lundberg & Woessner, P.A.

(57) ABSTRACT

A surgical device comprising: (1) a handpiece having a distal end portion; (2) a tubular member extending from the distal end portion, the tubular member having a lumen therethrough, the lumen comprising: (a) a proximal lumen portion, (b) a distal lumen portion, (c) a first central lumen portion, and (d) a second central lumen portion, the second central portion being located between the proximal lumen portion and the first central lumen portion, wherein the distal lumen portion diverges as the distal lumen portion extends away from the first central lumen portion in a distal direction, and the second central lumen portion diverges as the second central lumen portion extends away from the first central lumen portion in a proximal direction and: wherein the tubular member has wall with a substantially uniform thickness about the first central lumen portion.

13 Claims, 7 Drawing Sheets

Related U.S. Application Data

(60) Provisional application No. 62/319,359, filed on Apr. 7, 2016.

(51) Int. Cl.
 *A61B 17/29* (2006.01)
 *A61B 1/313* (2006.01)

(52) U.S. Cl.
 CPC .............. *A61B 17/29* (2013.01); *A61B 1/313* (2013.01); *A61B 1/3132* (2013.01); *A61B 2017/2901* (2013.01); *A61B 2017/2926* (2013.01); *A61B 2017/2933* (2013.01); *A61B 2017/2937* (2013.01)

(58) Field of Classification Search
 CPC ...... A61B 17/22031; A61B 2017/2926; A61B 2017/2933; A61B 2017/2937; A61B 2017/29012; A61B 2017/2932; A61B 2017/301; A61B 2017/303; A61B 2017/505; A61B 2017/12018; A61B 2017/00349; A61B 2017/22035; A61B 2017/2901; A61B 2017/2934; A61B 1/313; A61B 1/3132; A61B 1/00135; A61B 18/1447; A61C 3/16; A61C 3/14; B25B 9/04; B25B 9/00; B25B 7/00; B25B 7/205; B25B 23/10; G04D 1/02; G04D 1/021; A45D 26/0066
 See application file for complete search history.

(56) References Cited

U.S. PATENT DOCUMENTS

| | | | |
|---|---|---|---|
| 3,404,677 A | 10/1968 | Springer | |
| 3,920,021 A | 11/1975 | Hiltebrandt | |
| 3,934,589 A | 1/1976 | Zimmer | |
| 3,967,625 A | 7/1976 | Yoon et al. | |
| 4,003,380 A | 1/1977 | Wien | |
| 4,005,714 A | 2/1977 | Hiltebrandt | |
| 4,016,881 A | 4/1977 | Rioux et al. | |
| 4,054,143 A | 10/1977 | Bauer | |
| 4,418,692 A | 12/1983 | Guay | |
| 4,427,014 A | 1/1984 | Bell et al. | |
| 4,458,598 A | 7/1984 | Bornand | |
| 4,655,219 A | 4/1987 | Petruzzi | |
| 5,222,973 A | 6/1993 | Sharpe et al. | |
| 5,258,006 A | 11/1993 | Rydell et al. | |
| 5,318,589 A | 6/1994 | Lichtman | |
| 5,342,359 A | 8/1994 | Rydell | |
| 5,423,814 A | 6/1995 | Zhu et al. | |
| 5,445,638 A | 8/1995 | Rydell et al. | |
| 5,458,598 A | 10/1995 | Feinberg et al. | |
| 5,464,408 A | 11/1995 | Duc | |
| 5,496,317 A | 3/1996 | Goble et al. | |
| 5,499,997 A | 3/1996 | Sharpe et al. | |
| 5,527,313 A | 6/1996 | Scott et al. | |
| 5,595,186 A | 1/1997 | Rubinstein et al. | |
| 5,618,589 A | 4/1997 | McFarland | |
| 5,626,595 A | 5/1997 | Sklar et al. | |
| 5,638,827 A | 6/1997 | Palmer et al. | |
| 5,735,849 A | 4/1998 | Baden et al. | |
| 5,800,449 A | 9/1998 | Wales | |
| 5,972,002 A | 10/1999 | Bark et al. | |
| 6,113,596 A | 9/2000 | Hooven et al. | |
| 6,190,386 B1 | 2/2001 | Rydell | |
| 6,270,497 B1 | 8/2001 | Sekino et al. | |
| 6,464,702 B2 | 10/2002 | Schulze et al. | |
| 6,802,843 B2 | 10/2004 | Truckai et al. | |
| 9,216,030 B2 | 12/2015 | Fan et al. | |
| 10,631,836 B2 | 4/2020 | Batchelor et al. | |
| 2005/0216036 A1* | 9/2005 | Nakao .................. | A61B 17/083 606/139 |
| 2006/0224178 A1 | 10/2006 | Cheng | |
| 2006/0293696 A1 | 12/2006 | Fahey et al. | |
| 2009/0093675 A1* | 4/2009 | Surti ................... | A61B 1/00135 600/114 |
| 2011/0054462 A1 | 3/2011 | Ellman | |
| 2011/0087070 A1 | 4/2011 | Tilson et al. | |
| 2013/0090624 A1 | 4/2013 | Munsinger | |
| 2013/0197536 A1 | 8/2013 | Singh et al. | |
| 2015/0105821 A1 | 4/2015 | Ward et al. | |
| 2017/0290574 A1 | 10/2017 | Batchelor et al. | |

FOREIGN PATENT DOCUMENTS

| | | |
|---|---|---|
| WO | WO-2016027523 A1 | 2/2016 |
| WO | WO-2017177098 A1 | 10/2017 |

OTHER PUBLICATIONS

"U.S. Appl. No. 15/481,841, Corrected Notice of Allowability dated Mar. 11, 2020", 2 pgs.
"U.S. Appl. No. 15/481,841, Examiner Interview Summary dated Sep. 5, 2019", 4 pgs.
"U.S. Appl. No. 15/481,841, Non Final Office Action dated May 31, 2019", 18 pgs.
"U.S. Appl. No. 15/481,841, Notice of Allowance dated Dec. 18, 2019", 9 pgs.
"U.S. Appl. No. 15/481,841, Preliminary Amendment filed Oct. 2, 2018", 7 pgs.
"U.S. Appl. No. 15/481,841, Response filed Aug. 29, 2019 to Non Final Office Action dated May 31, 2019", 14 pgs.
"U.S. Appl. No. 15/481,841, Supplemental Notice of Allowability dated Feb. 25, 2020", 2 pgs.
"European Application Serial No. 17718460.3, Communication Pursuant to Article 94(3) EPC dated May 14, 2020", 7 pgs.
"International Application Serial No. PCT/US2017/026537, International Preliminary Report on Patentability dated Oct. 18, 2018", 7 pgs.
"International Application Serial No. PCT/US2017/026537, International Search Report dated Jul. 13, 2017", 4 pgs.
"International Application Serial No. PCT/US2017/026537, Written Opinion dated Jul. 13, 2017", 5 pgs.
"PKSTM Cutting Forceps, with Cord, 33 cm, 10 mm, Part No. 921020PK", Surgical Product Catalog. Gyrus ACMI, (2008).
"PKSTM Cutting Forceps, with Cord, 33cm, 5 mm, Part No. 920005PK", Surgical Product Catalog, Gyrus ACMI, (2008).
"PKSTM HALO Cutting Forceps, 5 mm, Product No. HACF0533", [Online] Retrieved from the internet: <https://web.archive.org/web/20140725082039/http://medical.olympusamerica.com/products/forceps/halo-pks-hacf00533>, (Jul. 25, 2014).
"European Application Serial No. 17718460.3, Communication Pursuant to Article 94(3) EPC dated May 23, 2022", 6 pgs.
"European Application Serial No. 17718460.3, Response filed Sep. 15, 2020 to Communication Pursuant to Article 94(3) EPC dated May 14, 2020", 10 pgs.

* cited by examiner

LAPAROSCOPIC SURGICAL DEVICE WITH FLARED TUBE

CROSS-REFERENCE TO RELATED APPLICATIONS

This application is a continuation of U.S. patent application Ser. No. 15/481,841, filed on Apr. 7, 2017 and issued on Apr. 28, 2020 as U.S, Pat. No. 10,631,836, which claims the benefit of U.S. Provisional Application Ser. No. 62/319,359 filed. Apr. 7, 2016, the contents of which are incorporated herein by reference in their entireties.

FIELD

The disclosure relates to a surgical device including a tubular member with a flared shape and more specifically to a tubular member of a surgical device with a flared shape at a distal end and a substantially uniform wall thickness.

BACKGROUND

Typically, laparoscopic surgical devices may have had to balance competing constraints. The tubular member should be small enough to pass through a standard surgical cannula (not shown) or trocar, which are usually circular, yet should be as large as possible to provide as much strength and/or stiffness as possible. An unwanted consequence of the flaring of the distal end of the tube is that the distal end of the tube becomes wider than the rest of the tube. Several solutions have been used to try to maximize the diameter of the proximal section of the tube while minimizing the width of the distal end of the tubular member. One solution, is to flare out the distal end of the tube as necessary and compromise the strength and inner space of the tubular member by reducing its size. Another solution is to retain the outer diameter of the tube and compromise the effectiveness of the flared surface by limiting it to a very small flare or the very marginal improvement of only chamfering the distal interior edge. Yet another solution is to increase the wall thickness greatly so that there is may be a generous flare while retaining tube strength; but compromising the overall weight of the device and reducing the inner space of the tubular member.

What is needed is a laparoscopic surgical device with a tubular member having a distal end with a flared shape that does not increase the overall diameter of the tubular member, nor require a heavy thick-walled tube. It would be attractive to have a tubular member with a flared shape and a wall thickness of the tubular member is substantially uniform. What is needed is a central opening with a flare that opens, closes, or both an end effector that extends out of the tubular member.

SUMMARY

In the current teachings there may be a section of the tubular member between a proximal cylindrical section of the tubular member and the distal section of the tubular ember that is necked down to a smaller diameter than the proximal section. From this necked down section, the distal section flares outward. In this way the distal end of the tube (tube and tubular member may be used interchangeably herein) may be smaller than if the flared shape were to come straight off the proximal section of the tube; in fact the distal end may be smaller in diameter than the proximal section. The entire tube may be fabricated from a thin walled tube of uniform wall thickness. Manufacturing methods that utilize thin-walled tubes with a uniform wall thickness, such as an extruded tube, may be employed. To reduce the magnitude of the contact forces and mitigate possible damage, in previous designs the tubular member may be flared out (e.g., flare) the inner surface of the distal end of the tube so that the distal interior surface of the tube diverges away from a central axis of the tube in a distal direction. Stated another way, the tangent to the distal interior surface at the distal interior edge diverges from the central axis of the tube in a distal direction. The flare in the distal interior section in the present teachings is, in general, configured such that when the end effector arms are drawn into the tube the camming surfaces on the arms contact the distal interior surface and not the distal interior edge.

The disclosure meets one or more of the needs by providing: a surgical device (10), comprising: (1) a handpiece having a handpiece distal end; (2) a tubular member extending from the handpiece distal end, the tubular member having a lumen therethrough, the lumen comprising: (a) a proximal lumen portion, (b) a distal lumen portion, (c) a first central lumen portion, and (d) a second central lumen portion, the second central portion being located between the proximal lumen portion and the first central lumen portion, wherein the distal lumen portion diverges as the distal lumen portion extends away from the first central lumen portion in a distal direction, and the second central lumen portion diverges as the second central lumen portion extends away from the first central lumen portion in a proximal direction and, wherein the tubular member has wall with a substantially uniform thickness about the first central lumen portion.

The present teachings provide a surgical device comprising: (1) a handpiece including a distal end portion; (2) a tubular member protruding from the distal end portion of the handpiece, the tubular member having: (a) a longitudinal axis, (b) a distal end; (c) a wall having a uniform wall thickness; and (d) a lumen; the lumen being axisymmetric and the lumen comprising: (A) a proximal interior surface, (B) a distal interior surface terminating at a distal interior edge; (C) a first central interior surface positioned between the proximal interior surface and the distal interior surface, and wherein distal interior surface at the distal interior edge converges towards the longitudinal axis as the distal interior surface extends in a proximal direction, and the first central interior surface has a central opening having a cross-section with an area that is smaller than an area of any cross-sections of the distal interior surface and smaller than an area of any cross-section of the proximal interior surface.

The present teachings provide a surgical device comprising: (1) a handpiece having a distal end portion; (2) a tubular member protruding from the distal end portion of the handpiece, the tubular member comprising: (a) a proximal section, (b) a distal section, (c) a first central section located between the proximal section and the distal section, and (d) a distal end, the distal end of the tubular member having a distal interior edge with a first diameter, and distal exterior edge with a second diameter, the first central section having a first central interior surface with a third diameter; and the proximal section having an proximal section exterior surface, the proximal section exterior surface being a cylinder having a fourth diameter; wherein the first diameter is greater than the third diameter, and the fourth diameter is greater to the second diameter.

The present teachings provide: a tubular member for a surgical device comprising: a proximal section; having a proximal section interior surface and a proximal section exterior surface; a first central section having a first central section interior surface and a first central section wall; a distal section having: a distal interior edge and a distal exterior edge; wherein the tubular member is configured to be positioned between a surgical handpiece and an end effector; wherein the diameter of the first central section interior surface is less than the diameter of the proximal section interior surface and the diameter of the distal interior edge; and the diameter of the proximal section exterior surface is greater than the diameter of the distal exterior edge.

The present teachings provide a laparoscopic surgical device with a tubular member having a distal end with a flared shape that does not increase the overall diameter of the tubular member, nor require a heavy thick-walled tube. The present teachings provide a tubular member with a flared shape and a wall thickness of the tubular member is substantially uniform. The present teachings provide a central opening with a flare that opens, closes, or both an end effector that extends out of the tubular member.

DETAILED DESCRIPTION

Figure 1:
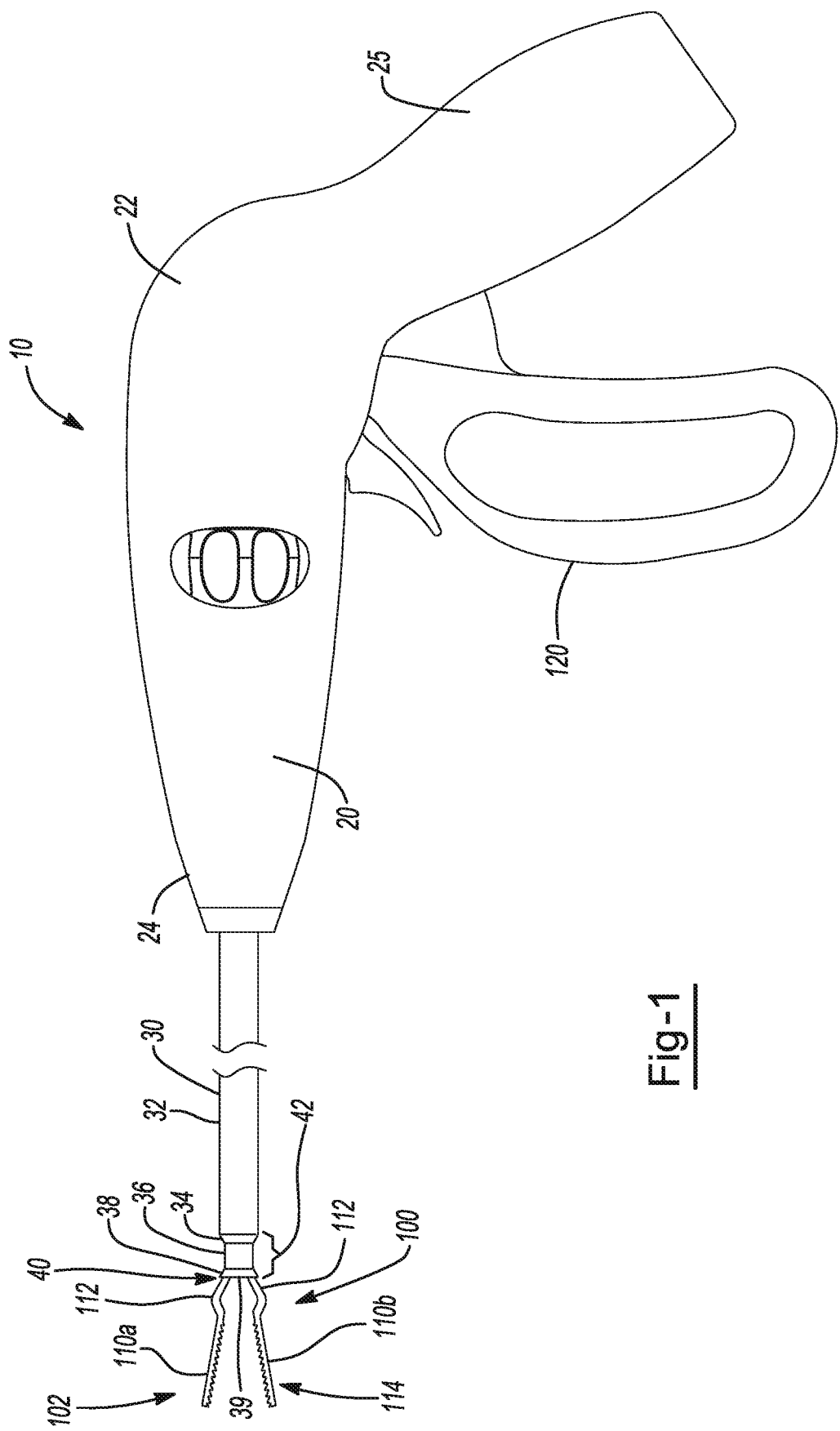
FIG. 1 shows a surgical device of the present teachings having a tubular member with two forceps arms in a first position.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings provide a surgical device. The present teachings provide a surgical device that may include a forceps device. The surgical device may have a handpiece, a tubular member, and an end effecter extending from the distal end of the tubular member. The surgical device has a handle or actuator that moves relative to the handpiece. The surgical device may by a handheld surgical device that may be intended to be held by the user, such as a surgeon, in one or both hands during normal operation. The surgical device may be a laparoscopic surgical device, and the laparoscopic device may include an end effector such as a laparoscopic forceps or laparoscopic scissors.

A typical laparoscopic surgical device may have a long cylindrical tube (e.g., tubular member) capable of being inserted through a trocar or cannula. The tubular member of the surgical device may be inserted through a trocar or cannula of a laparoscopic device or endoscope device. A portion of the surgical device may extend from a distal end of the trocar or cannula and the tubular member. Preferably, an end effector extends from the tubular member and the cannula or trocar. The trocar or cannula functions to assist the end effector to be guided to a location of interest and removed from the area of interest. Extending from the distal end of the tubular member may be an end effector that can be actuated to capture tissue, cut tissue, grip tissue, or a combination thereof. The proximal end of the tube may be attached to a distal end of the handpiece.

The handpiece may allow the user to hold the surgical device and to actuate user input controls that are converted by mechanisms held internal to the handpiece into specific surgical functions. Distal, or in a distal direction, means towards the intended patient and away from the user and proximal, or in a proximal direction, means away from the intended patient and towards the user. The handpiece may have a proximal end portion where is it is held by the user and a distal end portion. The tubular member, or shaft, may extend or project out of the distal end of the handpiece. The tubular member may be hollow and have a lumen that extends through the length of the tubular member from a proximal opening at the proximal end to a distal opening at the distal end. The tubular member may have a longitudinal axis that extends along the length of the tubular member. The tubular member may be straight, curved, or bendable. The longitudinal axis, therefore, may be straight or curved. The tubular member may include a wall, or tube wall. On the outer surface of the wall is an exterior surface of the tubular member and on the inner surface of the wall is the interior surface of the tubular member. The inner surface of the tubular member may create the lumen. The handpiece includes a proximal portion having a fixed handle that a user may grip. The fixed handle assists a user in biasing an actuator.

The actuator may move relative to the fixed handle. The proximal portion may include one or more actuators. The one or more actuators may actuate or bias one or more end effectors. The one or more actuators may actuate or bias the tubular member so that the one or more end effectors are actuated or biased by movement of the tubular member. The one or more actuators may cause the tubular member, the end effector, or both to move relative to each other. The actuator may be move in a handle closing direction, a handle opening direction, or both. The actuator in the handle closing direction may move the end effector to a second position or effector closing direction. The actuator in the handle opening position may move the end effector to a first position or an effector opening direction. The one or more actuators may actuate or bias one or more operable mechanisms that bias or actuate the tubular member, the end effector, or both. The operable mechanism may push on the tubular member, the end effector, or both. The operable mechanism may pull the tubular member, the end effector, or both. The operable mechanism may be located in or between the proximal end portion, the distal end portion, or both of the handpiece. The operable mechanism may include a spring. The operable mechanism may push the tubular member, may pull on the end effector, pull on a shaft connected to the end effector, or a combination thereof. The handpiece has an actuator to open and close the end effector arms. The actuator drives an operable mechanism may comprise a pivoting handle that creates relative motion between the end effectors and the tubular member. The distal end portion may receive an end of the tubular member or a portion of the tubular member. The distal end portion of the handpiece may remain outside of the cannula or trocar. The distal end portion of the handpiece may connect the operable mechanism, the actuator, or both to the end effector so that the end effector can be actuated.

The one or more end effectors function to assist a user in performing a surgical procedure. The end effectors may include a plurality of arms, jaws, or both. The end effectors may grip, cut, or both an object or tissue. The end effector may vary from procedure to procedure. The end effector may be scissors, forceps, a multi-arm forceps, or a combination thereof. The end effector may have jaws at the distal end of the tube that are open in their neutral state (e.g., in a first position) and can be closed to grasp tissue by the user (e.g., when moved to a second position). The end effector may include a pivot so that the arms of the end of the effector extend in opposing directions and rotate about the pivot. The arms may rotate toward each other about the pivot when the arms are moving from the first position to the second position. The one or more end effectors may include one or more camming surfaces. Each of the arms preferably include a single camming surface. The camming surface may be a surface that contacts the tubular member when the end effector is changed from a fist position to a second position. The camming surfaces may be a raised surface on an arm. The camming surfaces may be a portion of the arm that contacts the flare, the distal end, the restriction region, or a combination thereof. The camming surfaces may be contacted when the end effector is moved by an operable mechanism. A jaw actuation mechanism (e.g., operable mechanism) may advance the tube distally. The actuator has a first position and a second position. The actuator may drive an operable mechanism that may open and close the end effector arms. When the actuator is in the first actuator position the operable mechanism may drive the tubular section proximal relative to the end effector arms, may drive the end effector arms distal relative to the tubular member, or both. The distal end of the tubular member may move proximal relative to the end effectors.

The jaws of the end effector may have laterally extending sections that are wider than the mouth of the tube. When in the open state, the one or more arms of the end effector may extend wider than the distal opening of the tubular member. As the tubular member is advanced, the tubular member may gather the one or more arms of the end effector and force the arms towards each other, thereby closing the jaws. When the plurality of arms are closed the plurality of arms are brought into opposition with each other (i.e., are moved directly towards each other (e.g., like scissors about a pivot or like forceps that move in a same direction as forces on the forceps arms)). To open the end effector the user may relax the grip on the clamp lever and a spring (e.g., operable mechanism) may drive the jaw actuation mechanism towards its neutral position (e.g., first position) or an operable member may advance the end effector relative to the tubular member. As the tube is retracted or the end effector is advanced, the resilient nature of the arms may bias the arms of the end effector to return to their neutral, open state (e.g., first position).

The end effector may be comprised of a plurality of arms. The surgical device may be a forceps, an electrosurgical forceps, scissors, or other surgical device. The end effector may be configured to be drawn into the distal opening of the tubular member, or the tubular member may be configured to be extended to overrun the proximal portion of the end effector, so that one, more than one, or all of arms of the end effector may be driven from an open position, wide enough to grasp or approximate tissue, towards a closed position or into opposition with one or more of the other arms. The closed position (e.g., second position) may be a position where tissue is grasped, as in a forceps, or for cutting tissue, as in a scissors. There may be an actuator, or mechanism, in the handpiece to produce the relative motion between the tubular member and the end effector. The tubular member may terminate at its distal end at a distal interior edge and a distal exterior edge and the end effector may contact the tubular member at the distal interior edge or the distal exterior edge. A flare may be located at the distal end that assists in operating the end effector.

The flare in the distal interior section is, in general, configured such that when the end effector arms are drawn into the tube the camming surfaces on the arms contact the distal interior surface and not the distal interior edge. The flare may extend straight away from a longitudinal axis extending through the tubular member. The flare may include a conical surface that curves towards the longitudinal axis as the flare extends in the distal direction. The flare may include a concave portion, a convex portion, a straight portion, or a combination thereof. The flare may be linear. For example, the flare may have a cylindrical shape. In another example the flare may extend straight from an inflection point. The flare may be a curve. The flare may be smaller than the proximal section, second central section, first central section, or a combination thereof of the tubular member. The flare may be larger than the proximal section, second central section, first central section, or a combination thereof of the tubular member. The flare may have a concave portion and a convex portion. The flare or a curve of the flare may begin at an inflection point (e.g., a point where the slope of a wall changes). The curvature of the flare may be relative to a line that extends tangential to a point along the flare, a distal section, or both.

A degree of the curvature of the flare may be measured from a line tangent to a point along a curve of the flare. For example, a tangent line may extend thought a point of the curve and an angle of the tangent line may be measured relative to the longitudinal axis. The tangent line may extend through a center or midpoint of the curve. The tangent line may extend through a midpoint of a distal section wall. Preferably, the tangent line may extend through a midpoint of a curve of the distal section wall. The distal section wall may include one or more curves and thus may include one or more tangent lines. For example, the distal section wall may include a concave curve (e.g., outward curvature) and a convex curve (e.g., inward curvature) separated by an inflection point and each of the concave curve and the convex curve may have a tangent line with an angle relative to the longitudinal axis. A tangent line may extend through the distal interior edge, distal exterior edge, or both. The tangent line that extends through the distal interior edge, the distal exterior edge, or both may determine how a terminal end (e.g., distal end) extends. For example, the angle of the tangent line that extends through the distal interior edge, the distal exterior edge, or both determines the amount of flare at the end of the tubular member. The angle of the tangent line through the curve, the distal interior edge, the interior edge, or a combination thereof may have an angle of about 10 degrees or more, about 25 degrees or more, about 40 degrees or more, or even about 50 degrees or more. The angle of the tangent line through the curve, the distal interior edge, the interior edge, or a combination thereof may have an angle of about 85 degrees or less, about 75 degrees or less, or about 65 degrees or less. The curve may have an inward curvature (e.g., the curve extends from the internal wall outward) or the curve may be an outward curvature (e.g., the curve extends from the outward or external wall inward). When the wall has an external curvature then a line tangent to the distal interior edge may have the largest angle. For example, when the wall has an external curvature as the wall extends distal the wall may continually extend away from the longitudinal axis. The angle of the tangent line through the curve may be greater than the angle of the tangent line though the distal interior edge, the distal exterior edge or both. The angle of the tangent line through the curve may be less than the angle of the tangent line though the distal interior edge, the distal exterior edge or both. The angle of the tangent line through the curve may have a difference in angle of about 2 degrees or more, 5 degrees or more, or about 7 degrees or more relative to the tangent line though the distal interior edge, the distal exterior edge or both. The angle of the tangent line through the curve may have a difference in angle of about 25 degrees or less, 15 degrees or less, or about 10 degrees or less. The flare may be located at the distal end of the tubular member and may assist in expanding and retracting an end effector. The flare may be a portion of a wall of the tubular member and the flare may be located in a distal end region of the tubular member. The flare may be located proximate to a restriction region.

The tubular member may function to allow one or more end effectors to extend to a location of interest. The tubular member may open an end effector, close an end effector, or both. The tubular member may include a proximal section, distal end, second central section, proximal opening, central opening, first central section, distal section, distal opening, or a combination thereof. Each of the proximal section, distal end, second central section, proximal opening, central opening, first central section, distal section, distal opening, or a combination thereof may include a substantially uniform wall thickness (e.g., each of the wall sections may vary in thickness by less than 1 mm, preferably less than 0.1 mm). Each of the proximal section, distal end, second central section, proximal opening, central opening, first central section, distal section, distal opening, or a combination thereof may be formed of a single piece of material so that the tubular member is one solid unitary piece. Each of the sections may be formed in a solid tubular member.

The proximal section may extend from the handpiece. The proximal section may function to connect a tubular member to a handpiece. The proximal section may extend from a proximal end towards a distal end. The proximal section may extend to a restriction region. The proximal section may connect to a second central section. The proximal section may have a uniform wall thickness, uniform diameter, or both along a length of the proximal section. The proximal section may be a longest section of the tubular member. The proximal section may extend towards the distal end and into contact with the second central section or a first central section.

The second central section may function to taper the proximal section. The second central section may have diameter that is less than the proximal section. The second central section may have a diameter (e.g., a fourth diameter) that is different than the proximal section. The second central section may extend towards a longitudinal axis. The second central section may taper to an in inflection point. The second central section may extend to a distal end, a distal section, a first central section, or a combination thereof.

The first central section may function to a restrictive portion of the tubular member. The first central section may be a center of the restriction region. The first central section may extend parallel to the longitudinal axis. The first central section may have a wall that extends parallel to the proximal section. The first central section may terminate the taper of the second central section. The first central section may have a smallest diameter (e.g., third diameter) of the tubular member. The first central section may be located between the second central section and the distal section.

The distal section may function to terminate the tubular member. The distal section may include a flare. The distal section may extend outward from the longitudinal axis. The distal section may include one or more curves as discussed herein. The distal section may extend outward from the first central section. The distal section may include an outward curvature, an inward curvature, or both. The distal section may include any of the teachings herein as to the flare. The distal section includes a diameter. The dimeter of the distal section may be more than the second central wall, the first central section wall, the proximate section wall, or a combination thereof. The diameter (e.g., first diameter) may be less than the second central wall, the proximate section wall, or both. The diameter may be measured from an interior wall (e.g., first diameter) or from an exterior wall (e.g., second diameter). The distal section may terminate at a distal end of the tubular member. The tubular member includes a one or more openings and preferably a plurality of openings through the sections of the tubular member.

The proximal opening functions to permit an end effector to be connected with an actuator of the surgical device. The proximal opening may be a beginning or a lumen. The proximal opening may be located within the surgical device. The proximal opening may be connected to a central opening and a distal opening along a longitudinal axis of the tubular member. The proximal opening may be located at the proximal end or in a proximal end region. The proximal opening may and the central opening may be located adjacent.

The central opening may function to restrict an end effector. The central opening may be located at a distal end or in a distal end region. The central opening may be located within a restriction region. The central opening may be the opening that passes through the restriction region. The central opening may be located in the first central lumen portion, the first central section, within a first central exterior surface, or a combination thereof. The central opening may allow an end effector to pass out of the lumen and restrict a lumen being retracted into the lumen. The central opening may have a circular cross-section. The central opening may have a smallest diameter of the lumen within the tubular member. The central opening may have a smallest diameter of any of the cross-sections of the proximal interior surface. The central opening may be located proximate to the flare. The central opening may be located between the distal opening and the proximal opening. The central opening may be located adjacent to the distal opening.

The distal opening may have multiple increasing diameters. The distal opening may function to narrow as the distal opening extends proximally so that an end effector is restricted. The distal opening may have a gradually decreasing diameter as the distal opening extends proximally. Conversely, the distal opening may have a gradually increasing diameter as the distal opening extends distally. The distal openings may restrict the end effector when the end effector and the tubular member are moved toward each other. The distal opening may be located at a distal end of the tubular member. The distal opening, central opening, and the proximal opening may be located along the longitudinal axis.

The longitudinal axis may extend through a center of the tubular member, the lumen, or both. The longitudinal axis may extend from the distal end to the proximal end. The longitudinal axis may extend through a center of the tubular member despite changes in diameter of the tubular member along a length of the tubular member.

The tubular member may be a shaft that extends from the distal end of the handpiece. The shaft may be a wall. The tubular member may function to guide an end effector to a location of interest. The tubular member may function to protect an end effector during use. The tubular member may function to facilitate a contraction of an end effector (e.g., gripping or cutting). The wall of the tubular member may be one continuous piece that may include one or more and preferably a plurality of sections. The plurality of sections may all be part of a single wall. The wall may have a substantially uniform thickness along an entire length of the wall (e.g., the wall may vary in thickness by less than 1 mm, preferably less than 0.1 mm). The tubular member or the wall of the tubular member may comprise a proximal section wall, a distal section wall, a first central section wall located between the proximal section wall and the distal section wall, a second central section wall located between the proximal section wall and the first central section wall, or a combination thereof.

The proximal section wall may function to connect the tubular member to the handpiece of the surgical device. The proximal wall section may have a portion that extends into the handpiece and a portion that extends out of the handpiece. The proximal wall section may define a majority of the tubular member (e.g., 50 percent or more, about 60 percent or more, about 70 percent or more, or even about 90 percent or more of the tubular member along a length of the tubular member). The proximal section may have a continuous diameter from the handpiece to the second central section wall.

The second central section wall functions to change a diameter of the tubular member relative to the proximal section wall, the first central wall, the distal section wall, or a combination thereof. The second central section wall may be located between the proximal section wall and the second central section wall. The second central wall may be cylindrical or conical. The second central wall may be straight, linear, curved, concave, convex, or a combination thereof when viewed in the cross section. The second central wall may have decrease the diameter as the second central wall extends distally, towards the first central wall, or both. The second central wall may begin the restriction region when facing in a distal direction. The second central wall may transition from the proximal section to the first central section wall.

The first central section wall may function to restrict an end effector. The first central section may have a smallest diameter of any section. The first central section may have a constant diameter. The first central section wall may be located between the second central section wall and the distal section wall. The first central section wall may be cylindrical. The first central section wall may be a central part of the restriction region. For example, the first central section wall may form about 25 percent or more, about 40 percent or more, or about 50 percent or more of the restriction region by length. The first central section may connect to the distal section wall.

The distal section wall may be a wall that has the flare as is discussed herein. The distal section wall may have a diameter that varies as the wall extends distally. The distal section wall may contact the end effector when the tubular member and the end effector are moved relative to each other. The distal section wall may restrict the end effector so that the end effector moves from an open state to a closed state. The distal section wall may curve outward from the first central section wall. The distal section wall may be conical, cylindrical, include one or more curved sections, or a combination thereof. The distal section wall may include one or more concave curves, one or more convex curves, or both. The distal section wall may include one or more inflection points that change a slope, shape, or both of the distal section wall. The distal section wall may be straight, linear, curved, concave, convex, or a combination thereof when viewed in the cross section. The distal section wall includes an interior surface and an exterior surface.

The distal exterior surface and the distal interior surface function to define the outside of the wall and the wall thickness. The distal exterior surface and the distal interior surface may be parallel substantially along their length. The distal exterior surface, the distal interior surface, or both may include one or more chamfers, one or more fillets, one or more rounded portions, or a combination thereof. The distal exterior surface, the distal interior surface, or both may be free of chamfers, fillets, or both. The distal exterior surface and the distal interior surface may diverge at least along a portion of the distal exterior surface and the distal interior surface. The distal exterior surface and the distal interior surface may converge at least along a portion of the distal exterior surface and the distal interior surface. The distal interior surface may transition smoothly (e.g., free of sharp breaks or angles (i.e., a curve) from the first central interior surface to the distal interior edge. The distal interior surfaced may transition smoothly from the first diameter to the third diameter. The distal exterior surface and the distal interior surface may terminate at a distal exterior edge or a distal interior edge respectively.

The distal exterior edge, the distal interior edge, or both may function to be a terminal end of the tubular member. The distal exterior edge, the distal interior edge may be circular. The distal exterior edge, the distal interior edge may include one or more chamfers, one or more fillets, or both. The distal exterior edge, the distal interior edge may be separated by a thickness of the wall. The distal exterior edge and the distal interior edge may be at one end of the tubular member and the proximal section exterior surface and the proximal section interior surfaces may be located at opposing ends of the tubular member.

The proximal section exterior surface and the proximal section interior surface may extend generally parallel, determine a wall thickness, or both. Similarly all of the exterior surfaces and the interior surfaces may extend generally parallel to each other. The interior surfaces and the exterior surfaces may determine a diameter of the tubular member at a specific location. For example, the dimeter of the lumen may be measured from an interior surface to an interior surface and a diameter of the tubular member may be measured from an exterior surface to an exterior surface.

The tubular member may be a hollow tube having an interior surface and an exterior surface and a wall, or tube wall, extending between the interior surface and the exterior surface. The interior surface of the tube, the exterior surface of the tube and the tube wall may have portions that correspond to the proximal section, distal section, first central section, and second central section of the tubular member. There may be a proximal tube wall in the proximal section of the tubular member or about the proximal lumen portion. There may be a distal tube wall in the distal section of the tubular member or about the distal lumen portion. There may be a first central tube wall in the first central section of the tubular member or about the first central lumen portion. There may be a second central tube wall in the second central section of the tubular member or about the second central lumen portion.

The tubular member may include a lumen that extends through the tubular member. The lumen may function to permit the end effector to extend from the proximal end and the distal end. The lumen may have a plurality of portions. The lumen may have portions corresponding to the section of the tubular member. Specifically, the lumen may have a proximal lumen portion, a distal lumen portion, a first central lumen portion between the proximal lumen portion and the distal lumen portion, a second central lumen portion between the proximal lumen portion and the first central lumen portion, or a combination thereof.

The tubular member may be axisymmetric meaning that the interior surface and exterior surface are defined by circular cross-sections centered on the longitudinal axis of the tubular member. The interior surface cross-section and exterior surface cross-section may be concentric, (i.e., have the same center). Each section of the tubular member may be axisymmetric. The entire lumen or any portion of the lumen may be axisymmetric. Different cross-sections of the interior surface (and thereby lumen) or exterior surface may have circular cross-sections of different diameters.

The tubular member may be a straight tube with a centrally extending linear axis and an axisymmetric exterior surface and axisymmetric interior surface that defies an axisymmetric central lumen. The proximal section of the tube may have a cylindrical interior surface (proximal lumen portion) and a uniform wall thickness; and thereby a cylindrical exterior surface. The proximal section of the tubular member may be a cylinder and the first central section of the tubular member may be necked down to a smaller diameter, and the distal section of the tubular member flared outwardly. The distal portion of the lumen may diverge away from the first central portion of the lumen, or from the longitudinal axis, in a distal direction. The second central lumen portion may diverge away from the first central portion of the lumen, or from the longitudinal axis, in a proximal direction.

The distal interior surface may be conical. A cone is a surface produced by revolving a line about a coplanar and non-parallel axis. A cone is an axisymmetric surface that does not have curvature along its length. The distal interior surface may have outward curvature. That is the distal interior surface may diverge from the central axis faster, or at a steeper angle, at the distal end of the distal interior surface than it does a more proximal position of the distal interior surface. The angle between the central axis and a tangent to the distal interior surface at the distal end of the tube may be greater than the angle between the central axis and a tangent to the distal interior surface at a point proximal from the distal end of the tube. The distal interior surface may have inward curvature. That is the distal interior surface may diverge from the central axis more slowly, or with a shallower angle, towards its distal end than at a position that is proximal to the distal end. The angle between the central axis and a tangent to the distal interior surface at the distal end of the tube may be less than the angle between the central axis and a tangent to the distal interior surface at a point proximal from the distal end of the tube. The distal interior surface may have both portions with outward curvature and portions with inward curvature. There may be a curvature inflection point between portions with different curvature. The distal interior edge may be chamfered or it may be free of chamfers. Surfaces that have are smooth and have outward curvature may include a circular toroid or a toroidal toroid. The distal interior surface may transition smoothly (i.e. without discontinuities) along its length from the first central interior surface to the distal interior edge. The distal interior surface may include a fillet surfaces that transition without discontinuities to the first central interior surface.

The conical distal interior surface may be the flare. The conical distal interior surface may extend outward relative to a longitudinal axis as the conical distal interior surface extends distally. The conical distal interior surface may be the same as the distal interior surface but with a curvature. The conical distal interior surface may curve outward (i.e., outwardly curved distal interior surface), inward (i.e., inwardly curved distal interior surface), or both. When an outwardly curved interior surface and an inwardly curved interior surface are present they are separated by an inflection point (e.g., a curvature inflection point). The outwardly curved interior surface may be a surface where the wall bows inward towards the longitudinal axis. The outwardly curved interior surface may be in the distal end region, within the flare, or both. The outwardly curved interior surface may change slope from an inflection point so that the curve of the wall extends inward towards the longitudinal axis. The inwardly curved interior surface may be a surface where the wall bows outward away from the longitudinal axis. The inwardly curved interior surface may be in the distal end region, within the flare, or both. The inwardly curved interior surface may change slope from an inflection point so that the curve of the wall extends outward away from the longitudinal axis.

The first central section of the tubular member may have a cylindrical interior surface, or first central lumen portion, and a uniform wall thickness. Both of the first central lumen portion and the proximal lumen portion may be cylinders, with the first central portion having a smaller diameter than the proximal portion. The two cylinders may be coaxial. The second central lumen portion may be a surface that provides a smooth transition (i.e. without discontinuities) from the first central lumen portion to the proximal lumen portion. The second central interior surface may include fillet surfaces that transition without discontinuities to the first central interior surface and/or the proximal interior surface.

The first central interior surface, or first central lumen portion may, have a narrowest section, or central opening, that has a cross-section (e.g., perpendicular to the longitudinal axis) with an area smaller than the area of any cross-sections of the distal interior surface, the area of any cross-section of the second interior surface, and the area of any cross-sections of the proximal interior surface. The first central interior surface the distal interior surface, the second central interior surface, and the proximal interior surface may be axisymmetric, so the cross-sectional areas may correlate to diameters. The distal interior edge may be a circle. Therefore, the central opening may have a diameter smaller than the diameter of any cross-sections of the distal interior surface (including the distal interior edge), the second interior surface, and the proximal interior surface.

The first central lumen portion may be axisymmetric. The distal lumen portion may be axisymmetric and may extend distally from the distal end of the first central lumen portion; the distal lumen portion may diverge away from the central axis such that the cross section of the distal lumen portion has a greater diameter than the first central lumen portion, or the narrowest portion (central opening) of the first central lumen portion. The distal interior surface, or distal lumen portion, may terminate at a distal end of the tubular member at a distal interior edge. The second central lumen portion may be axisymmetric and may extend proximally from the proximal end of the first central lumen portion; the second central lumen portion may diverge away from the central axis in a proximal direction such that the cross section of the distal portion of the lumen has a greater diameter than the narrowest portion of the first central portion of the lumen. The proximal lumen portion may extend proximally from the proximal end of the second central lumen portion. The proximal lumen portion may be a cylinder with a diameter greater than either, or both of, the first central lumen portion (or its narrowest cross-section) and distal interior edge.

The surgical device may have a tubular member that extends from the distal end of the handpiece. The tubular member may have a proximal section, a distal section, a first central section and a distal end. At the distal end of the tube there may be distal interior edge and a distal exterior edge. The tubular member may be axisymmetric so that the distal interior edge and distal exterior edge are circular with first and second diameters, respectively. The first central section may have a first central interior surface with a third diameter. The proximal section may have a proximal section exterior surface that is a cylinder with a fourth diameter. The first diameter may be greater than the third diameters; i.e. the distal interior surface is flared outwardly, and the fourth diameter may be greater than the second diameter; i.e. the proximal exterior surface is wider than the distal end of the tube. The tube may have a uniform wall thickness along the first central section, of along the entire length of the tube.

The tubular member may comprise a proximal section with a tubular cylindrical cross-section. The first central section may be necked down so that the distal interior surface may be flared without resulting in the distal exterior edge being greater in diameter than the proximal exterior surface. The distal exterior edge may be chamfered or it may be free of chamfers.

The distal interior edge may have a chamfer. The chamfer on the distal interior edge may remove a sharp edge that could otherwise score or cut the end effector arm, or deteriorate the distal end of the tube. The distal exterior edge may have a chamfer. The chamfer on the distal exterior edge may remove a sharp edge that could otherwise score or cut the user or patient tissue. Alternatively the chamfer on the distal exterior edge may reduce the diameter of the distal exterior edge to provide clearance with the surgical cannula.

The distal end may be planar. The distal end may be non-planar. The distal end may be planar and non-perpendicular with respect to the longitudinal axis. In any case, the distal interior surface diverges away from the longitudinal axis in a distal direction at the distal interior edge.

The tubular member may have a uniform wall thickness about the first central lumen portion. The tubular member may have a uniform wall thickness about the first central lumen portion, as well as a uniform wall thickness of the same thickness about the distal lumen portion, the second central lumen portion, the proximal lumen portion, or any combination thereof. Each of the tube wall sections may have a uniform wall thickness along its length. Any two or more of the tube wall sections may have the same uniform wall thicknesses along their lengths. All of the tube wall section may have the same uniform wall thickness along their lengths. The tubular member may have a uniform wall thickness along its entire length.

A tube of uniform wall thickness along its length may have the benefit of being fabricated relatively easily from a single integral portion of extruded tube stock. The tubular member may be a single integral piece. A tubular member with an axisymmetric shape may have the benefit of not requiring specific orientation with the handpiece or the mechanisms that may extend the length of the tube to connect the end effector to mechanisms in the handpiece. An axisymmetric tube may not require any specific orientation with a surgical cannula through which the tubular member may be extended. The tubular member may be metal or plastic.

FIG. 1 illustrates a surgical device 10 including a handpiece 20 and a tubular member 30. The handpiece 20 includes fixed handle 25 and an actuator 120 that is movable relative to the fixed handle 25. The handpiece 20 includes a proximal end portion 22 located proximate to the fixed handle 25 and a distal end portion 24 of the handpiece 20 connects the tubular member 30 to the handpiece 20. The tubular member 30 includes a proximal section 32 that has a portion connected to the handpiece 20 and a portion that extends distally and connects to a second central section 34. The second central section 34 forms a transition between the proximal section 32 and the first central section 36. The first central section 36 connects the second central section 34 and the distal section 38 of the tube together. The distal section 38 extends distally and terminates at a distal opening 39 through which an end effector 100 extends out of the tubular member 30. The distal section 38 includes a flare 40 that extends outward relative to the first central section 36 that forms a restriction region 42 which assists in moving the end effector 100 between a first position and a second position. The end effector 100 as shown is forceps 102. The end effector 100 includes a first arm 110a and a second arm 110b. Each of the arms 110a, 110b include a camming surface 112.

The first arm 110a and the second arm 110b are shown in the first position 114 where the camming surface 112 is not being acted upon by the distal section 38 of the tubular member 30 so that the first working arm 110a and the second working arm 110b are spaced apart.

Figure 1A:
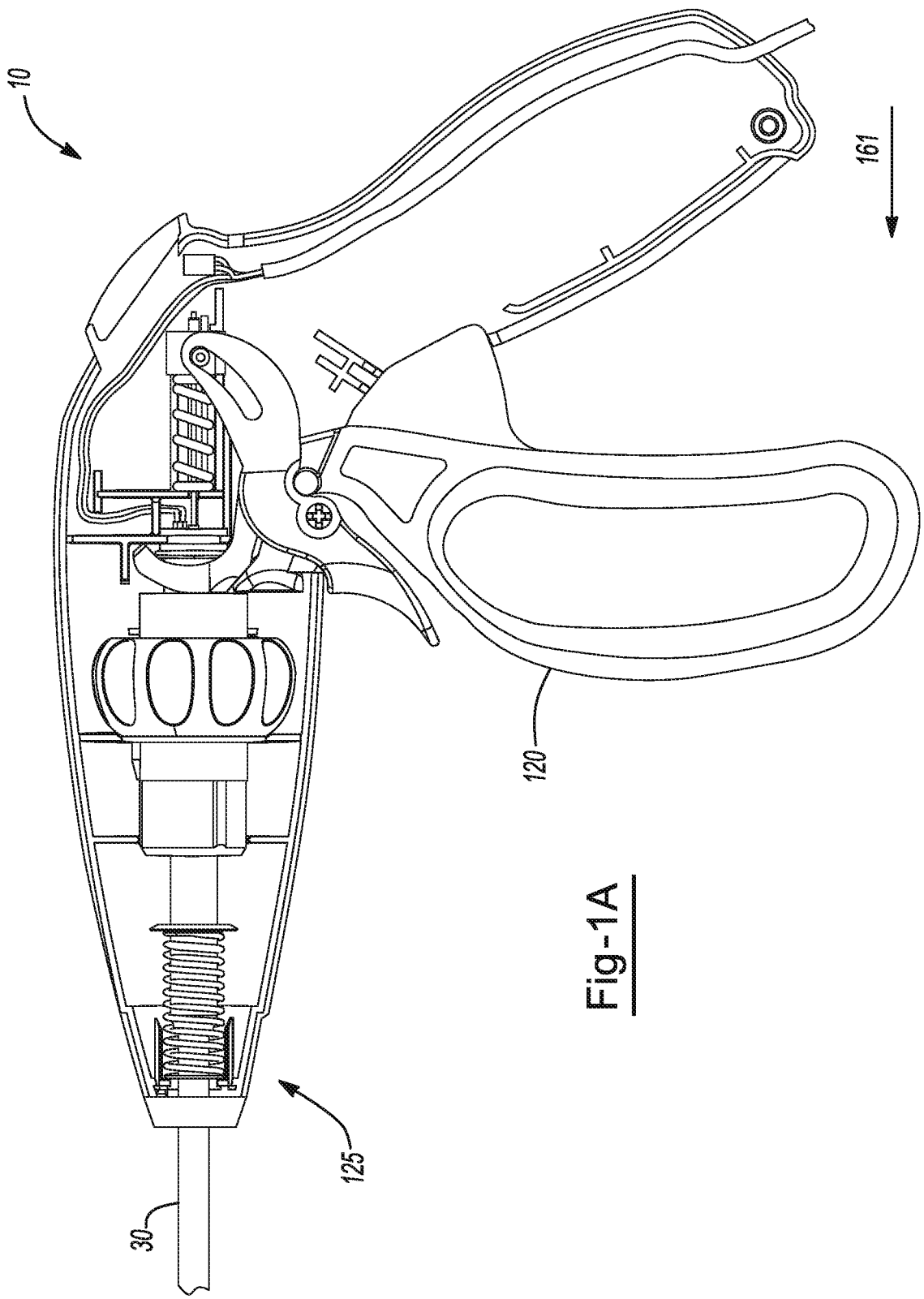
FIG. 1A is a top view of the surgical device with a top cover removed and the operable mechanism in a first position.

FIG. 1A illustrates the surgical device 10 with the actuator 120 moved in the handle opening direction 161. When the actuator 120 is in the first position the operable mechanism is in the first position and the tubular member 30 and the end effector (not shown) are moved relative to each other so that the end effector is open.

Figure 2:
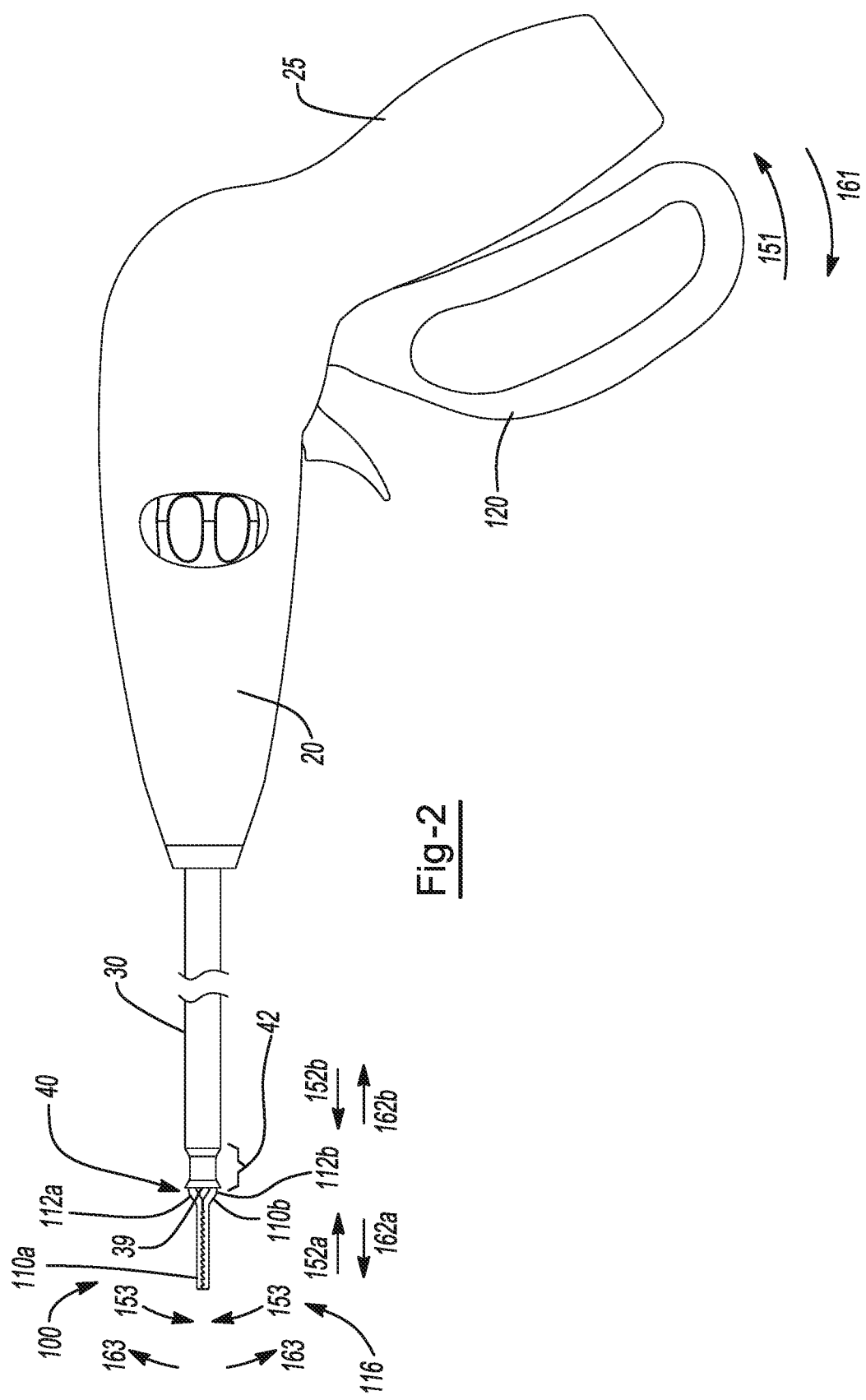
FIG. 2 shows a surgical device of the present teachings having a tubular member with two forceps arms in a second position.

FIG. 2 illustrates the surgical device 10 with the handpiece 20 and the tubular member 30 connected together. The handpiece 20 includes an actuator 120 that is connected to the end effector 100. When the actuator 120 is moved in the handle closing direction 151 towards the fixed handle 25, the end effector 100 and the tubular member 30 are moved relative in an contact direction (e.g., the tube may move (i.e., tubular contact direction 152b), the end effector may move (i.e., end effector contact direction 152a), or both) towards each other so that the camming surfaces 112 of the first working arm 110a and the second working arm 110b contact the distal opening 39 of the tubular member 30. During contact the camming surfaces 12 partially enter the flare 40 and then are restricted by the restriction region 42 so that the first working arm 110a and the second working arm 110b move toward each other in the effector closure direction 153 to a second position 116. Upon release of the actuator 120 the actuator moves in the handle opening direction 161 so that the tubular member 30 and the end effector 100 move relative to each other (e.g., the tube may move (i.e., tubular opening direction 162b), the end effector may move (i.e., end effector opening direction 162a), or both) so that the first arm 110a and the second arm 110b move apart in the direction 163.

Figure 2A:
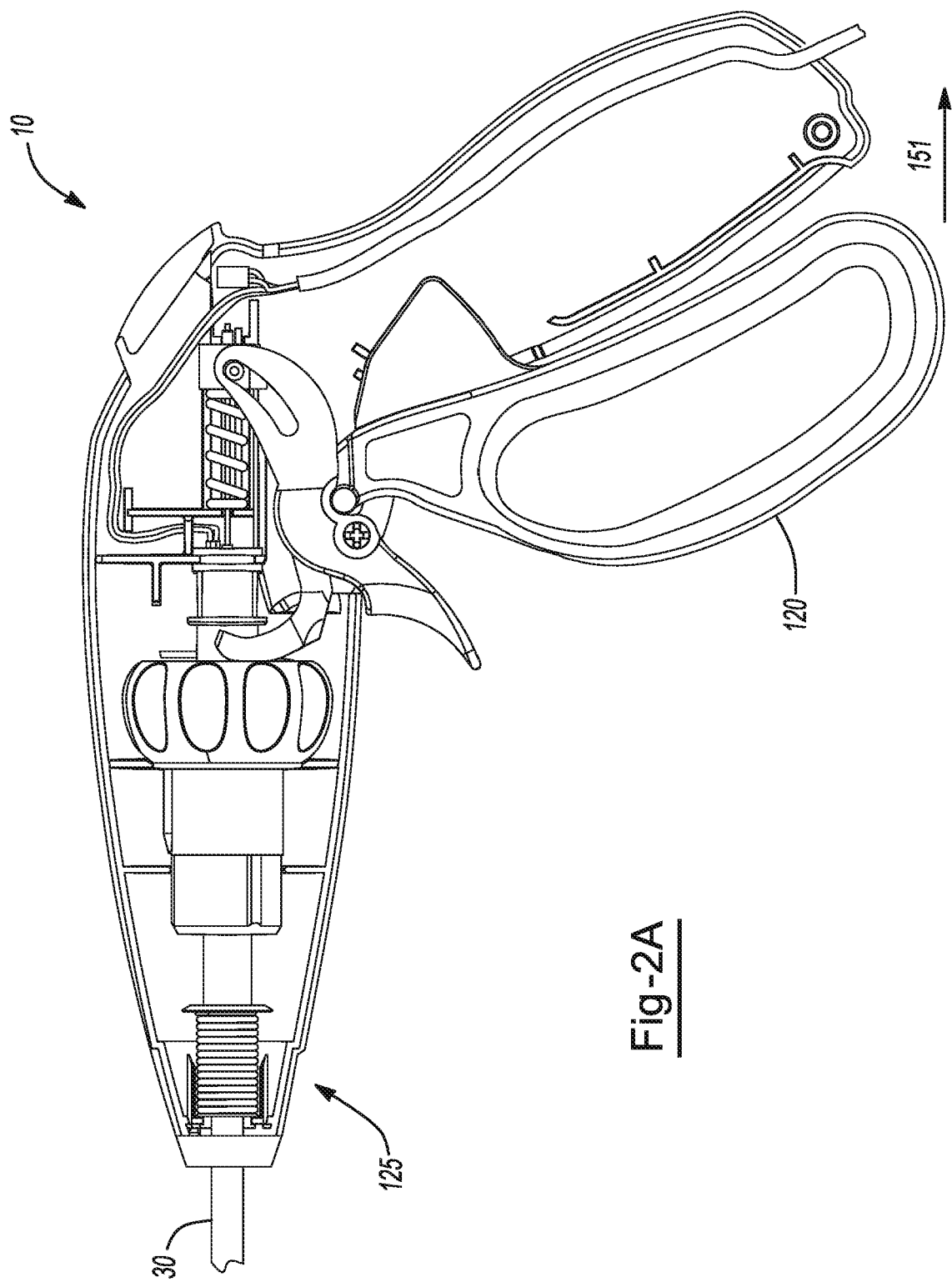
FIG. 2A is a top view of the surgical device with a top cover removed and the operable mechanism in a second position.

FIG. 2A illustrates the surgical device 10 with the actuator 120 moved in the handle closing direction 151. When the actuator 120 is in the second position the operable mechanism is in the second position and the tubular member 30 and the end effector (not shown) are moved relative to each other so that the end effector is closed.

Figure 3:
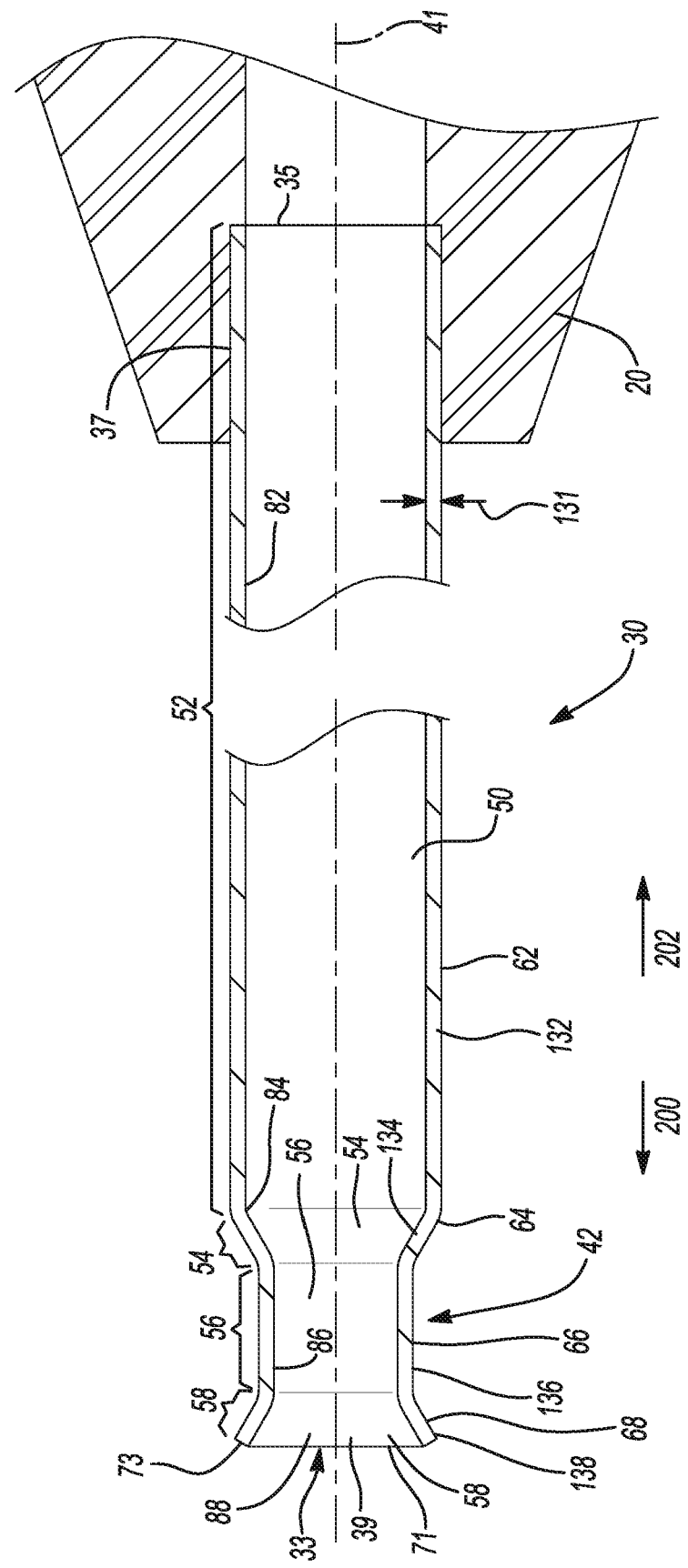
FIG. 3 shows a cross-section of the tubular member of the present teachings.

FIG. 3 illustrates a cross-sectional view of a tubular member 30 connected to the handpiece 20. The tubular member extends in a distal direction 200 and a proximal portion 202. A proximal end 37 of the tubular member 30 extends into the handpiece 20 to form a connection therebetween. The proximal end 37 includes a proximal opening 35 that begins a lumen 50 that extends the full length of the tubular member 30 along the longitudinal axis 41 and terminates at the distal end 33. The tubular member 30 includes a wall 131 with a wall thickness that is substantially uniform along an entire length of the tubular member 30. The wall 131 includes a proximal section wall 132 that adjoins with a second central section wall 134 that angles the proximal section wall 132 to the first central section wall 136. The first central wall section 136 is connected to a distal wall section 138 that angles outward creating a flare 40. The first central wall 136 forms a restriction region 42 between the distal section wall 138 and the second central wall section 134. Each of the sections of the wall 131 correspond to a related section of the lumen 50. The lumen 50 includes a proximal lumen portion 52 that extends partially into the handpiece 20 and distally to a second central lumen portion 54. The second central lumen portion 54 is connected to a first central lumen portion 56 that extends through the restriction region 42. The first central lumen portion 56 connects to the distal lumen portion 58 that is located within the flare 40 at the distal opening 39 of the tubular member 30. The tubular member 30 includes a plurality of interior and exterior surface that define the tubular member 30 and the lumen 50 within the tubular member. The proximal section wall 132 includes a proximal exterior surface 62 and a proximal interior surface 82. The second central section of the wall 134 includes a second central exterior surface 64 and a second central interior surface 84. The first central section wall 136 has a first central exterior surface 66 and a first section interior surface 86. The distal wall section 138 includes a distal exterior surface 68 and a distal interior surface 88. The wall 131 at the distal end 33 includes a distal interior edge 71 and a distal exterior edge 73.

Figure 4A:
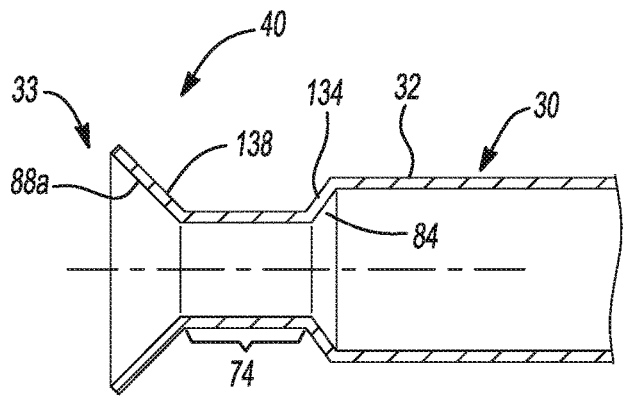
FIG. 4a show cross-section of the tubular member having a cylindrical central opening with a linear wall.

FIGS. 4a-4f illustrate various shapes and configurations of the distal end 33 of the tubular members 30 when viewed in in the cross-section. FIG. 4a shows the tubular members 30 with a central opening 74 and a distal wall section 138 that has a conical shaped distal interior surface 88a, and a second central wall 134 that has a conical second central interior 84. A flare 40 of the tubular member 30 extends outward and beyond the proximal section 32.

Figure 4D:
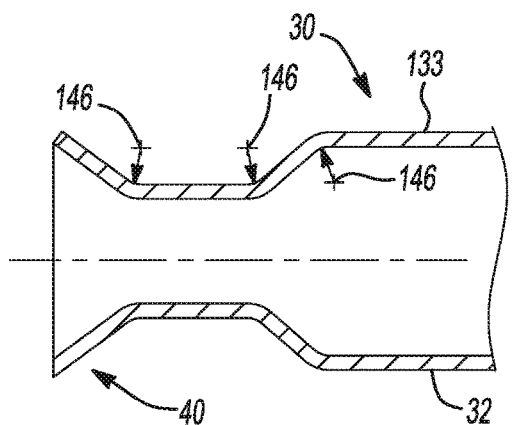
FIG. 4d shows fillets in the tubular member that form the central opening.
Figure 4B:
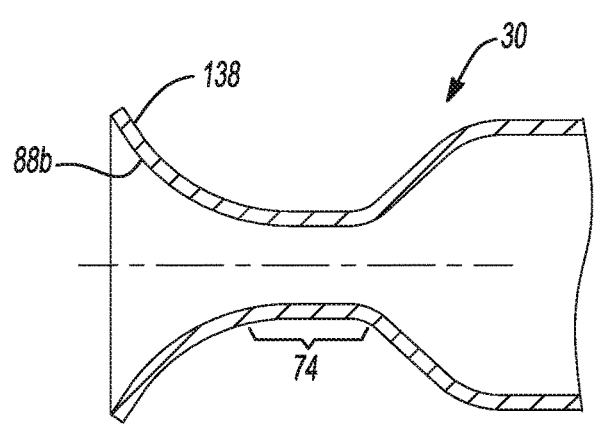
FIG. 4b shows a cross-section of the tubular member where a diameter of a distal exterior edge and a diameter of the proximal section of the tubular member are substantially equal.

FIG. 4b shows the tubular members 30 with a central opening 74 and a distal wall section 138 that has an outwardly curved distal interior surface 88b.

Figure 4E:
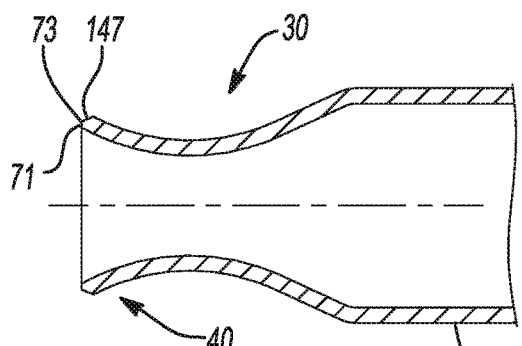
FIG. 4e shows a chamfer in the distal exterior edge of the tubular member.
Figure 4C:
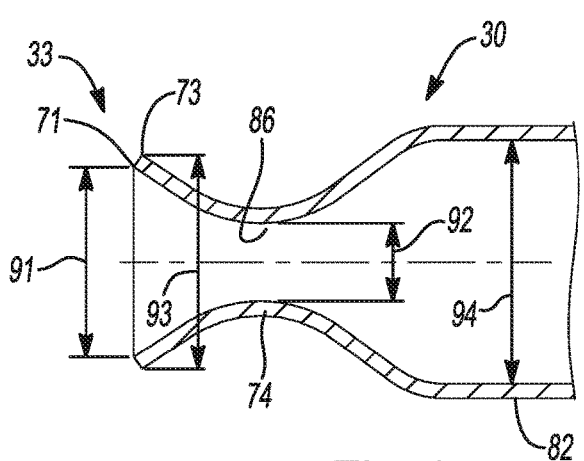
FIG. 4c shows a cross-section of the tubular member where a diameter of a distal exterior edge is less than a diameter of the proximal section of the tubular member.

FIG. 4c illustrates the changes in diameter of the tubular member 30. A distal opening 33 of the tubular member 30 has a first diameter 91 that extends between distal interior edges 71 as shown in the cross-section. The tubular member 30 has a third diameter 93 that extends between distal exterior edges 73 as shown in the cross-section. The tubular has a second diameter 92 within the central opening 74 and a fourth diameter 94 within the proximal section interior surface 82. The first central interior surface 86 in non-cylindrical.

FIG. 4d illustrates fillets 146 in the wall 131 at locations where the shape of the wall 131 change. A flare 40 of the tubular member 30 and the proximal section 32 are substantially equal.

FIG. 4e illustrates a chamfer 147 in the distal exterior edge 73 that extends from the distal exterior edge 73 towards the distal interior edge 71. A flare 40 of the tubular member 30 is smaller than the proximal section 32.

Figure 4F:
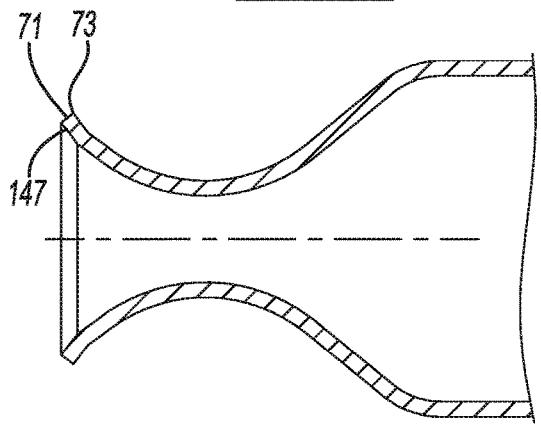
FIG. 4f shows a chamfer in the distal interior edge of the tubular member.

FIG. 4f illustrates a chamfer 147 in the distal interior edge 71 that extends outward towards the distal exterior edge 73.

Figure 5A:
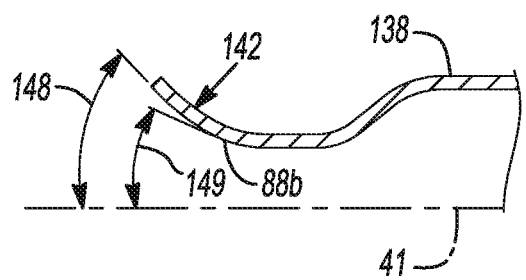
FIG. 5a shows a cross-section of the tubular member having an outwardly curved distal interior surface.
Figure 5B:
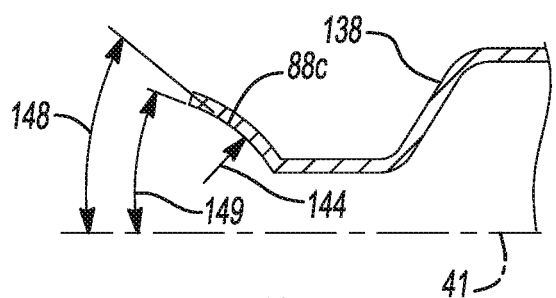
FIG. 5b shows a cross-section of the tubular member having an inwardly curved distal interior surface.
Figure 5C:
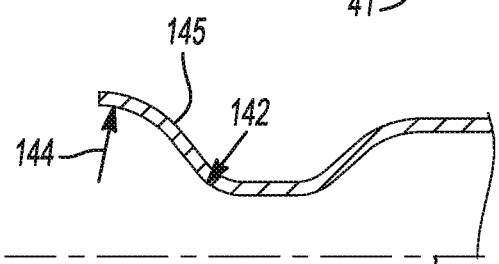
FIG. 5c shows a cross-section of the tubular member having an inwardly curved distal interior surface having an inwardly curved segment, an outwardly curved segment and a curvature inflection point.

FIGS. 5a-5c illustrate various configurations for the distal section wall 138. FIG. 5a illustrates the distal section wall 138 having an outward curvature 142 where the distal section wall 138 has an outwardly curved distal interior surface 88b. The outwardly curved distal interior surface 88b curves so that an angle of a line 148 tangent to the distal interior edge is greater than an angle of a line 149 tangent to a midpoint of the curve of the distal section wall 138 when measured relative to the longitudinal axis 41.

FIG. 5b illustrates the distal section wall 138 having an inward curvature 144 so that the distal section wall 138 has an inwardly curved distal interior surface 88c. The inwardly curved distal interior surface 88θ curves so that an angle of a line 148 tangent to the distal interior edge is less than an angle of a line 149 tangent to a midpoint of the curve of the distal section wall 138 when measured relative to the longitudinal axis 41.

FIG. 5c illustrated the distal section wall 138 includes an outward curvature 142 and an inward curvature 144 separated by an inflection point 145 where the curve of the distal section wall 138 changes.

Figure 6:
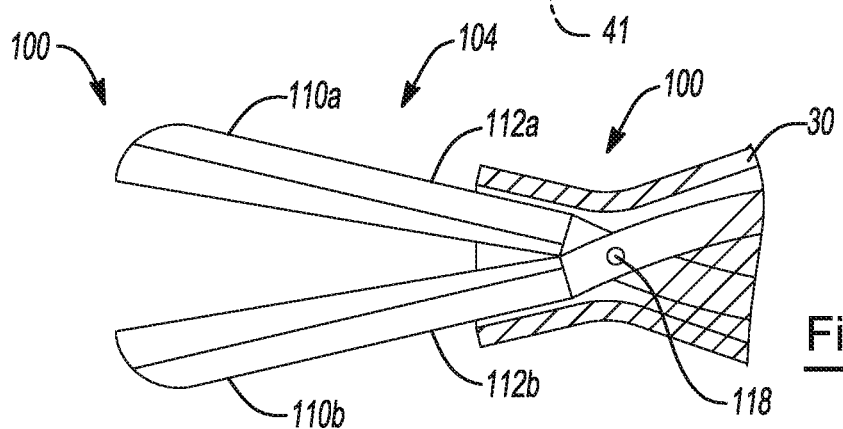
FIG. 6 shows a tubular member of the present teachings with an end effector extending therethrough.

FIG. 6 illustrates an end effector 100 extending from the tubular member 30. The end effector 100 has a first arm 110a and a second arm 110b that are connected at a pivot 118. The first arm 110a and the second arm 110b outward from the pivot point 118 so that the first arm 110a and the second arm 110b extend outward and are a camming surface 112a and 112b respectively that causes the first arm 110a and the second arm 110b to close upon contact with the tubular member 30. The end effector 100 as shown is scissors 104.

Figure 7:
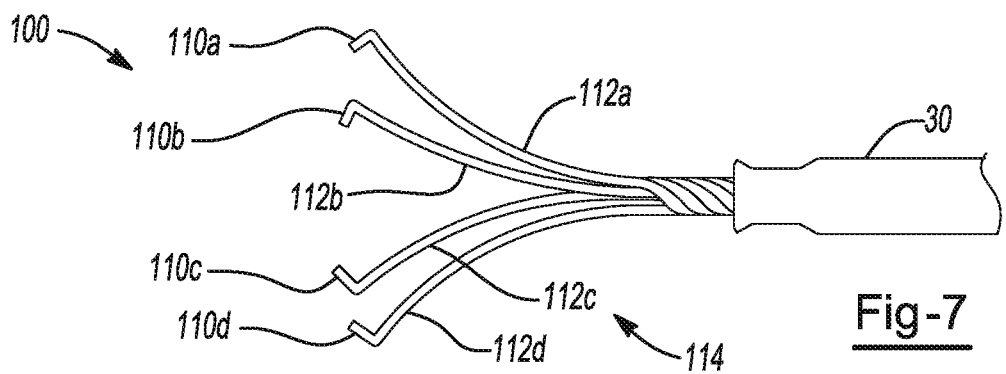
FIG. 7 shows a surgical device of he present teachings having a plurality of arms.

FIG. 7 illustrates an end effector 100 in a first position 114 extending from a tubular member 30. The end effector 100 includes a plurality of arms and each arm includes a camming surface. As shown, the first arm 110a has a first camming surface 112a, the second arm 110b has a second camming surface 112b, the third arm 110c has a third camming surface 112c and the fourth arm 110d has a fourth camming surface 112d.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

ELEMENTS

10 Surgical device
20 Handpiece
22 proximal end portion (of handpiece)
24 distal end portion (of handpiece)
25 fixed handle
30 tubular member
32 proximal section (of tube)
33 distal end (of tube)
34 second central section (of tube)
35 proximal opening (of tube)
36 first central section (of tube)
37 proximal end (of tube)
38 distal section (of tube)
39 distal opening (of tube)
40 flare
41 longitudinal axis (of tube)
42 Restriction region
50 Lumen
52 proximal lumen portion
54 second central lumen portion
56 first central lumen portion
58 distal lumen portion
62 proximal section exterior surface
64 Second central exterior surface
66 First central exterior surface
68 Distal exterior surface
71 distal interior edge
73 distal exterior edge
74 central opening
82 proximal interior surface
84 second central interior surface
86 first central interior surface
88 distal interior surface
88a conical distal interior surface
88b outwardly curved distal interior surface
88c inwardly curved distal interior surface
91 first diameter (distal interior edge)
92 third diameter (central opening)
93 second diameter (distal exterior edge)
94 fourth diameter (proximal section exterior diameter)
100 end effector
102 forceps
104 scissors
110a-d arms
112 camming surfaces (on the arms)
114 First position
116 Second position
118 pivot
120 Actuator
125 operable mechanism
131 wall (for tube)
132 proximal section wall
134 second central section wall
136 first central section wall
138 distal section wall
142 arrow (outward curvature)
144 arrow (inward curvature)

145 inflection point
146 Fillets
147 Chamfer
148 angle (tangent at distal interior edge)
149 angle (tangent at section proximal from distal interior edge)
151 handle closing direction
152a end effector contact direction
152b tubular contact direction
153 effector closure direction
161 handle opening direction
162a End effector opening direction
162b Tubular opening direction
163 arrow end effector opening movement
200 Distal direction
202 Proximal direction

We claim:

1. A surgical device, comprising:
a handpiece including a distal end portion;
a tubular member extending from the distal end portion, the tubular member including a lumen extending therethrough, the lumen comprising:
a proximal lumen portion including a proximal end that extends from the distal end portion of the handpiece;
a distal lumen portion;
a first central lumen portion; and
a second central lumen portion connected to and located between a distal end of the proximal lumen portion and a proximal end of the first central lumen portion;
wherein the distal lumen portion diverges along an entire length of the distal lumen portion as the distal lumen portion extends away from the first central lumen portion in a distal direction and terminates at a distal opening that forms a distal end of the tubular member, and the second central lumen portion diverges as the second central lumen portion extends away from the first central lumen portion in a proximal direction;
wherein the first central lumen portion is a hollow cylinder;
wherein the tubular member has wall with a uniform thickness about the distal lumen portion, the first central lumen portion, the second central lumen portion, and the proximal lumen portion; and
wherein a diameter of the distal inner edge is greater than a diameter of the first central lumen.

2. The surgical device of claim 1, wherein the lumen is axisymmetric about a longitudinal axis of the tubular member.

3. The surgical device of claim 1, wherein the diameter of the first central lumen portion is smaller than a diameter of the proximal lumen portion.

4. The surgical device of claim 1, wherein the proximal lumen portion has a cylindrical shape.

5. The surgical device of claim 1, wherein the tubular member is an integral piece.

6. The surgical device of claim 1, wherein the tubular member further comprises:
an end effector mounted within the lumen and partially extending from the distal end of the tubular member, the end effector comprising a plurality of arms, wherein at least one of the plurality of arms is movable from the first position where the plurality of arms are disposed in spaced relation relative to each other to the second position where the plurality of arms are brought into opposition with each other; and
an actuator for actuating movement of the at least one of the plurality of arms of the end effector between the first position and the second position.

7. The surgical device of claims 6, wherein the plurality of arms comprises a pair of arms.

8. The surgical device of claim 6, wherein the surgical device is a laparoscopic surgical device.

9. The surgical device of claim 6, wherein the end effector is configured to extend out of the distal end of the tubular member and the distal opening is smaller than the end effector so that when the end effector and the tubular member are moved into contact, the distal end of the tubular member overruns a proximal portion of the end effector driving the end effector from a first position to a second position.

10. The surgical device of claim 1, wherein the distal lumen portion has a distal exterior edge with a first diameter and the proximal lumen portion has a second diameter and the first diameter and the second diameter are equal.

11. A surgical device comprising:
a handpiece having a distal end portion;
a tubular member extending from the distal end portion of the handpiece, the tubular
member comprising:
a proximal section;
a distal section,
a first central section located between the proximal section and the distal section; and
a distal end including a distal interior edge defining a first diameter, and a distal exterior edge that is located at an exterior surface of the tubular member and terminates at the distal end of the tubular member, the distal exterior edge defining a second diameter;
wherein the first central section includes a first central interior surface defining a third diameter that is constant;
wherein the proximal section includes a proximal section exterior surface, the proximal section exterior surface being a cylinder defining a fourth diameter;
wherein the first diameter is greater than the third diameter and the second diameter is greater than the first diameter; and
wherein the tubular member has wall with a uniform thickness from the distal end to a proximal end of the proximal section.

12. The surgical device of claim 11, wherein the tubular member has a wall with a uniform wall thickness in the first central section.

13. The surgical device of claim 11, wherein the tubular member has a wall with a uniform wall thickness for an entire length of the tubular member.

* * * * *